US012626808B2

(12) United States Patent
Jussel et al.

(10) Patent No.: US 12,626,808 B2
(45) Date of Patent: May 12, 2026

(54) PROCESSING DEVICE FOR PROCESSING A DENTAL INDICATION

(71) Applicant: Ivoclar Vivadent AG, Schaan (LI)

(72) Inventors: Rudolf Jussel, Feldkirch-Gisingen (AT); Theresa Sujata Maria Senti, Triesenberg (LI)

(73) Assignee: Ivoclar Vivadent AG, Schaan (LI)

( * ) Notice: Subject to any disclaimer, the term of this patent is extended or adjusted under 35 U.S.C. 154(b) by 600 days.

(21) Appl. No.: 17/808,231

(22) Filed: Jun. 22, 2022

(65) Prior Publication Data

US 2023/0005606 A1 Jan. 5, 2023

(30) Foreign Application Priority Data

Jul. 1, 2021 (EP) ..................................... 21183074

(51) Int. Cl.
    *G16H 40/20* (2018.01)
    *G06K 19/06* (2006.01)
(52) U.S. Cl.
    CPC ....... *G16H 40/20* (2018.01); *G06K 19/06037* (2013.01)
(58) Field of Classification Search
    CPC ........ G16H 40/20; G16H 40/63; G16H 10/60; G06K 19/06037; G06K 17/00; G06K 19/06009; G05B 2219/45167; G05B 19/12; G05B 2219/23363; G05B 2219/36371; B23C 3/00
    See application file for complete search history.

(56) References Cited

U.S. PATENT DOCUMENTS

| | | | |
|---|---|---|---|
| D855,088 S | 7/2019 | Tinius | |
| 11,312,350 B2 | 4/2022 | Martin | |
| 2014/0028441 A1 | 1/2014 | Amran | |
| 2014/0140783 A1* | 5/2014 | Stine ................. | A61C 13/0006 |
| | | | 409/84 |
| 2014/0303755 A1 | 10/2014 | Landgraf et al. | |
| 2015/0144611 A1 | 5/2015 | Miller | |
| 2015/0227943 A1 | 8/2015 | Radomsky | |
| 2017/0315516 A1 | 11/2017 | Kozionov et al. | |
| 2018/0159937 A1 | 6/2018 | Stolzer et al. | |
| 2019/0130596 A1* | 5/2019 | Manafighazani .... | G06Q 10/087 |
| 2020/0397534 A1 | 12/2020 | Farrelly et al. | |
| 2021/0102527 A1 | 4/2021 | Liu et al. | |
| 2021/0178639 A1 | 6/2021 | Lukacs et al. | |

(Continued)

FOREIGN PATENT DOCUMENTS

| | | |
|---|---|---|
| CN | 111325835 A | 6/2020 |
| DE | 102019210085 A1 | 1/2021 |

(Continued)

OTHER PUBLICATIONS

Hay, Christian, "Barcode scanning in healthcare Towards better, more efficient and safer patient care," report, 8 pages, White Paper Barcode Scanning in Healthcare, Zebra Technologies, 2015.

*Primary Examiner* — Sonji N Johnson
(74) *Attorney, Agent, or Firm* — Ann M. Knab; Thad McMurray

(57) ABSTRACT

A processing device (100) for processing a dental indication (103), including an electronic status detection device (105) for detecting status data of the processing device (100) and/or the dental indication (103); and an electronic generation device (107) for generating a code (109) comprising the status data.

11 Claims, 4 Drawing Sheets

(56)                    References Cited

U.S. PATENT DOCUMENTS

| | | | |
|---|---|---|---|
| 2021/0191370 A1 | 6/2021 | Carlsson | |
| 2021/0196576 A1 | 7/2021 | Vinograd et al. | |
| 2021/0310903 A1 | 10/2021 | Emmert et al. | |
| 2022/0148717 A1 | 5/2022 | Yatim et al. | |
| 2022/0265882 A1 * | 8/2022 | Lemchen | .................. A61L 2/28 |

FOREIGN PATENT DOCUMENTS

| | | | | |
|---|---|---|---|---|
| EP | 3690572 A2 | 8/2020 | | |
| EP | 3699841 A1 | 8/2020 | | |
| JP | 2019216996 A | * 12/2019 | | |
| WO | WO-2006065409 A2 * | 6/2006 | ............. | A61C 13/16 |
| WO | WO-2006084079 A2 * | 8/2006 | ............. | A61C 19/02 |

* cited by examiner

PROCESSING DEVICE FOR PROCESSING A DENTAL INDICATION

CROSS-REFERENCE TO RELATED APPLICATIONS

This application claims priority to European Patent Application No. 21183074.0 filed on Jul. 1, 2021, the disclosure of which is incorporated herein by reference in its entirety.

TECHNICAL FIELD

The present invention relates to a processing device for processing a dental indication, a processing system including the processing device, and a method for processing a dental indication.

BACKGROUND

Currently, device information is managed manually when processing dental indications. A dental technician or dentist enters the data manually in the respective documentation tool or enters them on an order slip. This is tedious, time-consuming and error-prone. As a result, information in the processing procedure is often not or only insufficiently documented and passed on.

US 20210178639, 20210310903, 20210191370, 20210102527, 20180159937, 20170315516, 20140303755, 20140028441, 20150227943, 20200397534, and U.S. Ser. No. 11/312,350 are directed to devices and methods for monitoring machines and/or dental devices and are hereby incorporated by reference in their entirety. US 20220148717 and 20210196576 are directed to medical device and reporting systems and are hereby incorporated by reference in their entirety.

SUMMARY

It is the technical aim of the present invention to provide a processing device for processing a dental indication, with which relevant status or state data can be passed on and documented in a simple manner.

This technical problem is solved by objects according to the independent claims. Technically advantageous embodiments are the subject of the dependent claims, the description and the drawings.

According to a first aspect, the technical problem is solved by a processing device for processing a dental indication, comprising an electronic status or state detection device for detecting status or state data of the processing device and/or the dental indication; and an electronic generation device for generating a code comprising the status data. A dental indication is an artificially produced object used in a patient's mouth, such as a crown, a bridge, a full or partial denture, an aligner, a grinding splint, an implant, an abutment, or a telescopic prosthesis. The processing device is used to process or fabricate the dental indication in a technical process. The processing device achieves the technical advantage that the status data can be exchanged in a simple manner via the generated code and can be passed on to other devices.

In a technically advantageous embodiment of the processing device, the processing device comprises a display device for displaying the code. The display device is formed, for example, by an electronic matrix display. This achieves, for example, the technical advantage that the code can be read directly on the processing device.

In a further technically advantageous embodiment of the processing device, the display device is configured to display the code in an optically detectable or scannable manner. This provides, for example, the technical advantage that the code can be automatically read opto-electronically by another device having a camera or a scanner.

In a further technically advantageous embodiment of the processing device, the code is a bar code, a QR code, a text code or a machine-readable code. This achieves, for example, the technical advantage that the status data can be integrated into the code in an efficient and automatically detectable manner.

In a further technically advantageous embodiment of the processing device, the processing device comprises a data interface for electronically sending the code. The interface is, for example, a wireless or wired data interface for an electronic network, such as a network card or a WLAN interface. This provides, for example, the technical advantage that the code can be transmitted electronically directly to other devices.

In a further technically advantageous embodiment of the processing device, the processing device comprises a detection interface for optically detecting data of a manufacturing material. The detection interface is formed, for example, by an electronic camera for capturing an image and a corresponding scanning program for scanning the captured image. This achieves, for example, the technical advantage that data of used manufacturing materials can be captured in a simple and fast manner and can also be integrated into the code.

In a further technically advantageous embodiment of the processing device, the code comprises data on an identification number of the processing device, on a manufacturing material, on a number of operating hours, on a calibration performed, on a due date for the next calibration, on error messages and warnings, on statistics, on the programs or jobs used, on a running process, on a process parameter, on jobs processed during processing, on materials used during processing, on an installed software version and/or on error-free execution of a process. This achieves, for example, the technical advantage of integrating data for further processing steps or documentation steps into the code.

In a further technically advantageous embodiment of the processing device, the processing device is a dental or dental materials processing device including, but not limited to, a milling device, a 3D printer, a firing furnace, a press furnace, a sintering furnace, a scanner, a light curing device, a post-exposure device, a mixing system, a color measuring system, a polymerization device, a sterilization device, a dental technician handpiece or a cleaning device. This achieves, for example, the technical advantage of integrating data from dental machining processes into the code.

According to a second aspect, the technical problem is solved by a processing system comprising a processing device according to one of the first aspect; and a software application for receiving the code. The software application may be implemented on a mobile phone, a tablet PC, augmented reality glasses or a computer.

Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device. It may take the form of a computer program product comprising program code which is stored on a machine-readable medium, the machine-readable medium comprising computer instructions executable by a processor, which computer instructions cause the processor to perform the method described above. This achieves the technical advantage of being able to easily forward and process the code.

According to a third aspect, the technical problem is solved by a method for processing a dental indication, comprising the steps of detecting status data of the processing device and/or the dental indication; and generating a code comprising the status data. Thereby, the same technical advantages are achieved as by the processing device according to the first aspect.

In a technically advantageous embodiment of the method, the code is displayed optically or sent via a data interface. This achieves, for example, the technical advantage that the code can be transmitted quickly and easily.

In a further technically advantageous embodiment of the method, data on an identification number of the processing device, on a manufacturing material, on a number of operating hours, on a calibration performed, on a due date for the next calibration, on error messages and warnings, on statistics of the programs or jobs used, on a running process, on a process parameter, on jobs processed during processing, on materials used during processing, on an installed software version and/or on error-free execution of a process are recorded and/or embedded in the code. This also achieves, for example, the technical advantage that data for further processing steps or documentation steps are integrated into the code.

In a further technically advantageous embodiment of the method, the code is transmitted to a data node. The data node may be, for example, a local or remote computer, a mobile phone or a tablet. The data node is, for example, connected to the processing device via a data channel and can perform further processing steps based on the code. This achieves, for example, the technical advantage of integrating data for further processing steps or documentation steps into the code.

In a further technically advantageous embodiment of the method, the code is stored in an electronic patient file. The patient file can be stored in a digital manner centrally and decentrally, such as on an internet server or a local PC as a file or in a database. The patient file can be stored in a tamper-proof manner by digitally signing it using a cryptographic method or by storing it as a data record in a blockchain. This has the technical advantage, for example, of providing secure documentation for a dentist.

In a further technically advantageous embodiment of the method, a plausibility check is performed to determine whether a manufacturing material or machine parameters are suitable for a predetermined dental indication. In this plausibility check, it can be checked whether a manufacturing material is suitable for the processing device or a particular processing method. The result of this plausibility check can also be integrated into the code as status data. This achieves the technical advantage, for example, that errors in the machining process can be prevented or detected.

BRIEF DESCRIPTION OF THE DRAWINGS

Examples of embodiments of the invention are shown in the drawings and will be described in more detail below.

DETAILED DESCRIPTION

Figure 1:
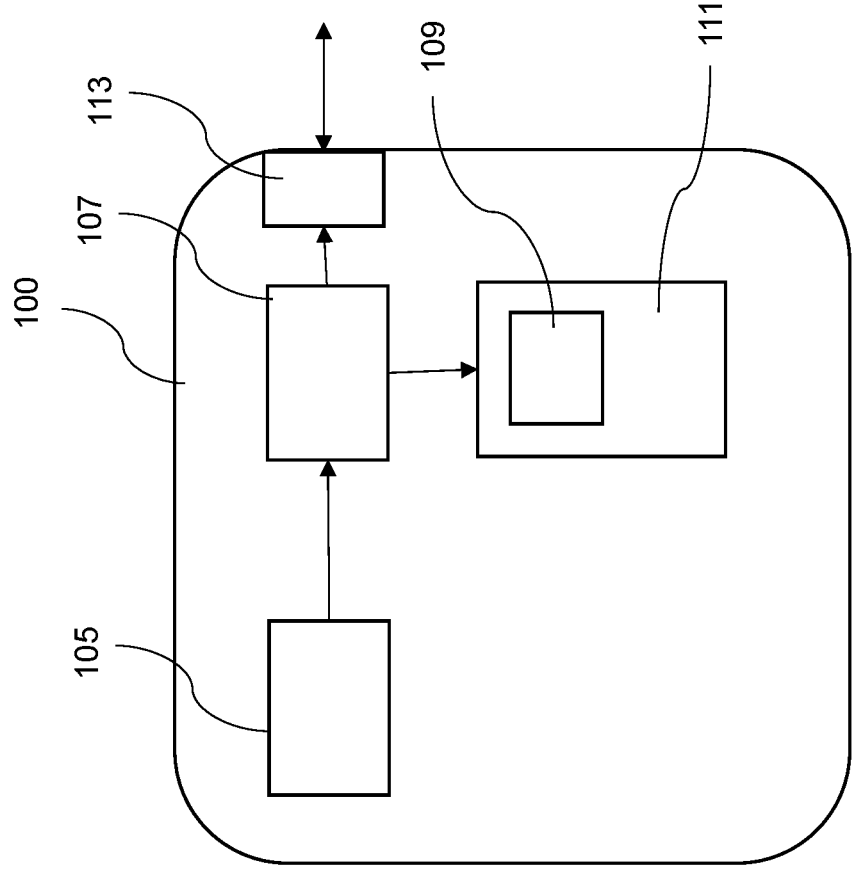
FIG. 1 shows a schematic representation of a processing device.
Figure 1:
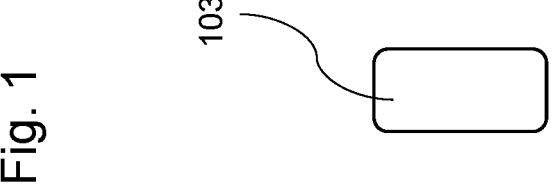

FIG. 1 shows a schematic diagram of a processing device 100. The processing device 100 is a device used as part of a processing method that produces or processes a dental indication 103. This may be, for example, including but not limited to, a milling device, a 3D printer, a firing furnace, a press furnace, a sintering furnace, a scanner, a light-curing device, a post-exposure device, a mixing system, a color measurement system, a polymerization device, a sterilization device, a dental technician handpiece, or a cleaning device for the dental indication 103.

The processing device 100 includes an electronic status detection device 105 for detecting status data of the processing device 100 and/or the dental indication 103 with suitable electrical circuitry and/or a sensor. In addition, the status detection device 105 may include one or more sensors for sensing the status data. The electrical circuitry may include the components and wiring needed to operate the particular sensors associated with the device, and/or to receive and process the output signals generated by the sensors. This circuitry can include, but is not limited to: analog and digital circuitry; CPUs; processors; circuit boards; memory; firmware; and controllers.

The status condition data may be, for example, static data of the processing device 100 or dynamic data of a machining process. For example, an internal identification number or a digital hour meter of the processing device 100 can be read by the electronic status detection device 105. Through the electronic status detection device 105, the time of a performed calibration of the processing device 100 can be determined. Digital information about error messages and warnings can be acquired by the electronic status detection device 105.

Statistics about programs or jobs in use, data about a machining process in progress, and/or process parameters may be detected by the electronic status detection device 105. In addition, data may be collected about jobs that are currently being processed or about manufacturing materials that are currently being used. In addition, the status detection device 105 may detect data about an installed software version and/or about an error-free execution of a process as status data. Further, data about the currently executing process may be detected as status data of the processing device 100, such as process parameters, processed objects/orders, loading status, material information. However, this information can generally also be added manually.

The status data thus detected is transmitted by the status detection device 105 to an electronic generation device 107, which dynamically generates a code 109 from the data. The code 109 contains the status data provided in each case. For example, the code 109 is a bar code, a QR code, a text code, or a machine-readable code generated by an appropriate algorithm based on the transmitted status data. For this purpose, the generation device 107 may be implemented by a microprocessor or by means of a digital circuit. The code 109 may be generated or displayed, for example, by pressing a button on the processing device.

The code 109 is then transmitted to and displayed on a display device 111. The display device may be, for example, an electronic display on which the code 109 is displayed as a QR code, bar code or text code. However, the code 109 may also be output on paper from a printer. From this display device 111, the code 109 may in turn be scanned by another electronic device, such as a mobile phone, tablet computer or augmented reality glasses. It is also possible for the code 109 to be passed in machine-readable form to another device via a digital data interface 113.

In principle, any processing device 100 having a suitable display device 111 for visually displaying the code 109 is suitable. If the resolution of the display device 111 is not large enough to display the code 109 with the appropriate information, the status data can also be divided into several smaller codes 109 which appear simultaneously or successively on the display device 111.

Figure 2:
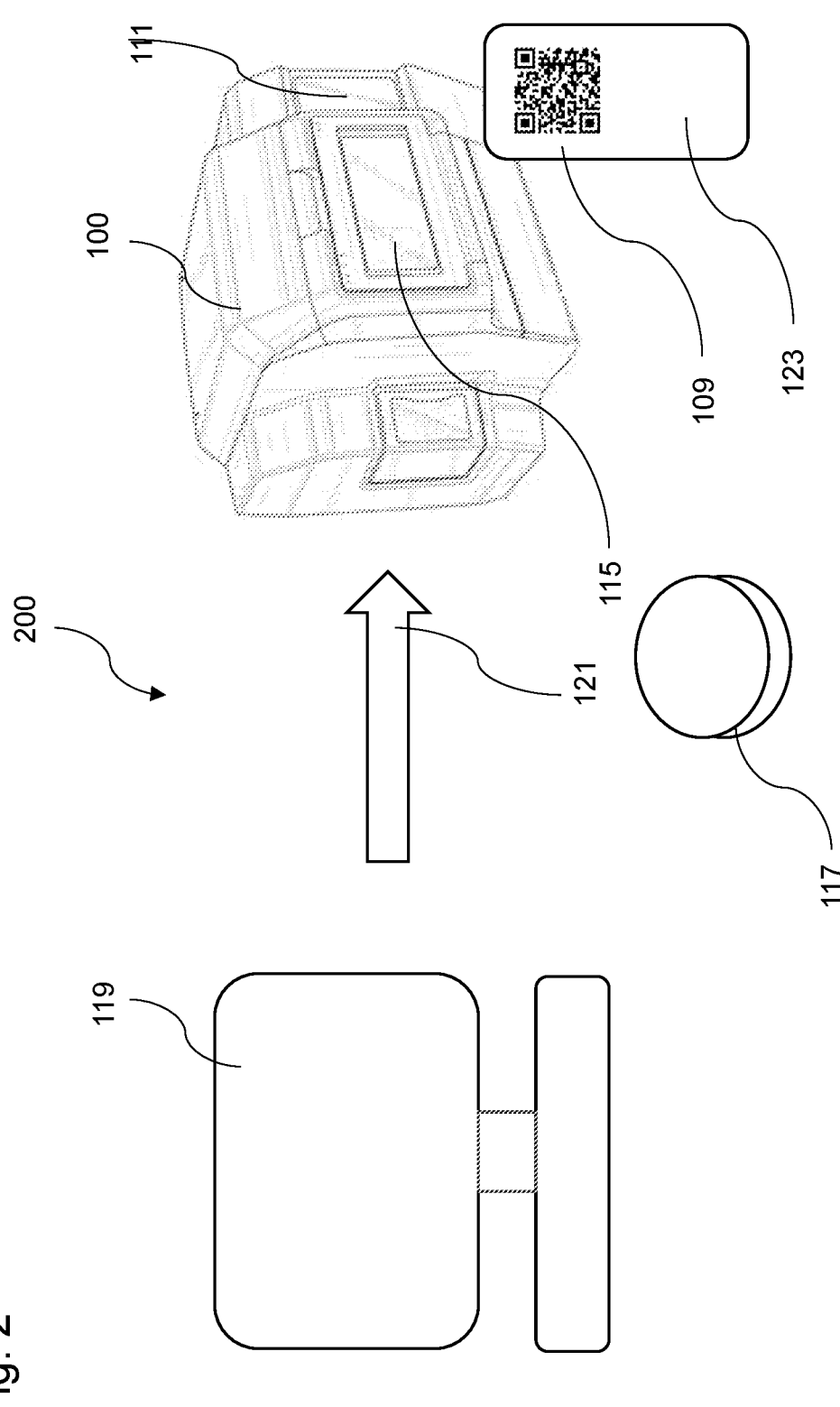
FIG. 2 shows an illustration of a manufacturing system including a processing device and a software application for receiving a code.

FIG. 2 shows an illustration of a processing system 200 including the processing device 100 and a software application for receiving the code 109. For example, the computer 119 includes software that allows the dental indication 103 to be designed by a user. Once the data set is completed at the computer 119, it is digitally transmitted to the processing device 100 via a data channel 121.

The processing device 100 processes the dental indication 103 based on the transmitted data set. In this process, the aforementioned condition data may be obtained. The code 109, in which the condition data is embedded, is generated by the generation device 107 and then visually displayed on the display device 111.

This code 109 can then in turn be optically read by a suitable device 123, such as a mobile phone, a tablet PC or AR glasses. This device 123 may then extract and further process the status data thus transmitted from the code 109. For example, a log containing manufacturing data of a device 123 dental indication 103 can be added to the list of processed dental indications.

In this regard, a plausibility check may further be performed in which the manufacturing material 117 is first detected. This may be done by an optical scanning process via a detection interface 115, which is used to capture the data of the manufacturing material 117. The detection interface 115 is formed, for example, by an electronic camera and image recognition software.

For example, the manufacturing material 117 may be identified in the following manner:

Character recognition on the label (product name, LOT number);

Coloring of the label or packaging;

Comparison of the label with a label retrieved from a database; and/or

Form of packaging.

Subsequently, a plausibility check is performed to determine whether the detected manufacturing material 117 is also suitable for the dental indication 103 and can be processed by the processing device 100 in the desired manner.

For this purpose, the respective machine parameters of the processing device 100 can be considered as status data. If the plausibility check runs with a positive result, processing is released by the processing device 100. The plausibility check status data thus obtained can also be embedded in the code 109. In addition, information about the manufacturing material 117 currently in use and other information known to the processing device 100 may be acquired and read out as status data, such as a device status including calibration, service and software update information and other measured values. This status data may also be stored in and embedded in the code 109.

Other status data may include, but is not limited to, information about:

a number to identify the respective processing device (IOS data, device number, software version, hardware version);

a device status;

a manufacturing material used (LOT number, material description, material information, layering process);

a number of operating hours of the processing unit;

a time (date/time) of the last calibration of the machining unit;

a time (date/time) when the next calibration is due;

a log of the processes, error messages and warnings;

statistics on the programs or orders used during processing;

an information about a currently running process or process parameter;

an order that is currently being processed;

patient Data;

agent data;

user Data;

manufacturer data (dental practice; dental laboratory);

an order description (type of dental indication, color, material; size; quantity);

a data format (STL—Standard Tessellation Language)

a CAM material information (designation, tools, LOT-No.);

a CAM device information (identification no., device status, calibration status);

CAM process information (milling strategy, build parameters, CAM software version);

a digital sample (color);

an opening status of a door of a milling chamber (open/closed);

an opening status of a valve (open/closed);

a tool status (present/broken); and/or a material status (present/inserted).

Sensor data may include information about:

physical quantities (speed, temperature, pressure, frequency);

chemical quantities;

derivatives of chemical or physical quantities over time (relative or absolute);

location data or position data;

an identification (RFID, barcode);

a status and signals (On, Off); and/or a time stamp.

Data formats of the sensors include:

numbers;

text;

image (2D, 3D);

video (gesture);

audio (speech); and/or status (True, False).

Tasks performed using the sensors or sensor data include:

control and planning;

tracking (track and trace);

visual Inspection;

documentation;

guide and help;

support (Support); and/or tools and features (Tools and Features, such as a magnifying glass).

If a process is performed without errors, the code 109 is only output at the end of the performed process. If the processing device 100 is no longer compliant, for example a calibration fails, a warning is output and code 109 is no longer displayed.

This enables simple and complete documentation of all relevant device parameters by capturing the dynamic and/or static code that contains all the required information.

In addition, an automatic electronic reordering of the used manufacturing materials 117 can take place or a risk management can be carried out on the basis of the status data. Statistics on orders and material consumption can be obtained. The status data provides traceability and traceability of the manufacturing process, for example based on batch numbers and a device status.

Figure 3:
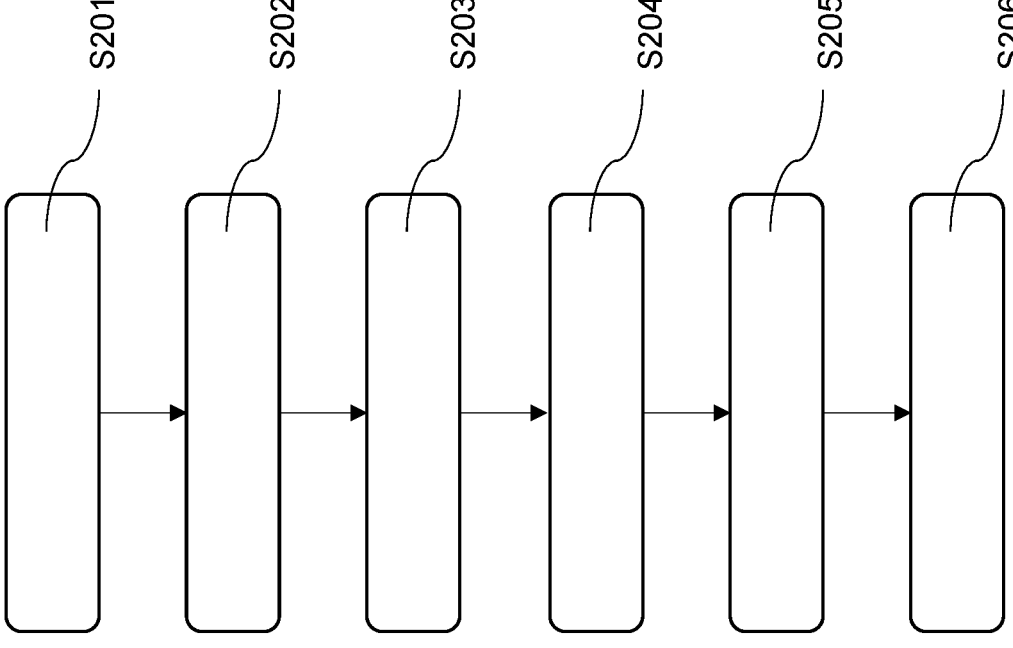
FIG. 3 shows a block diagram for an exemplary manufacturing process.

FIG. 3 shows a block diagram for an exemplary manufacturing process for a dental indication.

In step S201, patient data is first collected from the dentist, such as a jaw impression, intraoral scan or tooth shade, and an order is created for the dental technician. In addition to the patient data, the dental technician may contain further information about the material to be used, such as metal ceramics or zirconium oxide.

In step S202, this information is transferred from the dentist to the dental technician and documentation is created for the patient case or existing documentation from the dentist is reused. This may work, for example, if the dentist and the dental technician use shared software that allows the patient case to be documented together. This software can run on a mobile device such as a mobile phone, tablet PC or augmented reality (AR) glasses.

In step S203, the dental technician may, for example, design a dental crown as a dental indication 103 from zirconia based on the data on the computer, which is manufactured on a milling machine as a processing device 100. Upon completion of the fabrication, for example, a barcode may be displayed that includes information in the status data such as the selected material, the minimum wall thickness, and other parameters of the dental crown or processing device 100 as status data. This barcode can be scanned by the dental technician using a mobile phone, and the information can be added to the order using a documentation tool.

Further status data is generated on the milling machine during the manufacturing process. For example, the tools used and the material are detected. After completion of the milling process, this information and other information about the process, such as error messages or warnings that have occurred or a unique identification number of the milling machine, can be read in via a QR code and added to the order as status data via the QR code.

In step S204, the dental crown is separated from a block, ground and then sintered. In a sintering furnace, relevant information such as a unique identification of the sintering furnace, the selected sintering program, actually measured temperatures, error messages are again recorded and stored in the code 109.

In step S205, the restoration is further built up using the layering technique, for example. Materials used here, such as a ceramic powder, and the information on how they were fired can also be recorded. For this purpose, a QR code may be displayed on the sintering furnace with the information of the sintering furnace. The detection of the materials may be done via a QR code provided on the packaging or on the material itself, such as on the press blank. If no code is present, the material can be recognized by the following features or a corresponding combination:

Character recognition on the label (product name, LOT number);

Coloring of the label or packaging;

Comparison of the label with a database; and/or

Form of packaging.

In step S206, the information collected via code 109 is summarized in the documentation tool. This results in complete, secure, and paperless documentation of the respective dental indication, which can be provided to the dentist for insertion and (possibly to a reduced extent) for forwarding to the customer. The documentation can be integrated into an electronic patient file.

Figure 4:
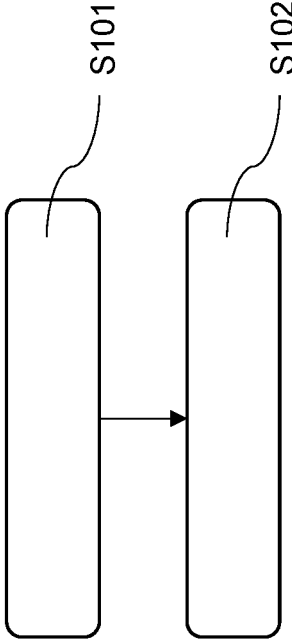
FIG. 4 a block diagram of a method for processing a dental indication.

FIG. 4 shows a block diagram of a method for processing the dental indication. In step S101, status data of the processing device and/or the dental indication is first detected. In step S102, the code 109 comprising the status data is electronically generated.

Existing processing devices 100 can also be subsequently integrated into the process by modifying the software for the purpose of data acquisition and documentation, without having to retrofit another interface. In principle, if the display device 111 for the code 109 is available, complex interface components can be dispensed with. This can also be advantageous if battery-operated machining equipment is to operate in a consumption-optimized manner. In order to integrate an older processing device 100 into the method, only a software update is required in which it is defined which information is stored in the code 109, the size of the code 109, the basic design of the code 109 and when the code 109 is displayed.

The method can be used for a documentation requirement in all medical fields and thus also in the dental field for the dentist and at the dental technician, since the status data of the processing device 100 play an important role here, with which the dental indication 103 is processed. In addition, a time saving results for a simple and complete documentation of the status data.

The method can also be used for processing devices 100 that do not have an interface for integration to higher-level systems. However, the processing devices 100 can be integrated via an interface, such as wireless (WLan or Bluetooth) or via cable (Lan), via which a transmission of the code to a higher-level system takes place.

Alternative possibilities include the processing device 100 maintaining a log file that provides information about the processing of jobs, or outputting a document for paper-based documentation via a connected printer when a job is processed.

All of the features explained and shown in connection with individual embodiments of the invention may be provided in different combinations in the subject matter of the invention to simultaneously realize their beneficial effects.

All method steps can be implemented by devices suitable for executing the respective method step. All functions that are executed by the subject features can be a process step of a method.

In some embodiments, a computing device may include one or more processor(s), one or more memory device(s), one or more interface(s), one or more mass storage device(s), and one or more Input/Output (I/O) device(s), all of which are coupled to a bus. Processor(s) include one or more processors or controllers that execute instructions stored in memory device(s) and/or mass storage device(s). Processor(s) may also include various types of computer-readable media, such as cache memory.

In some embodiments, memory device(s) may include various computer-readable media, such as volatile memory (e.g., random access memory (RAM)) and/or nonvolatile memory (e.g., read-only memory (ROM)). Memory device(s) may also include rewritable ROM, such as Flash memory.

In some embodiments, mass storage device(s) may include various computer readable media, such as magnetic tapes, magnetic disks, optical disks, solid state memory (e.g., Flash memory), and so forth. Various drives may also be included in mass storage device(s) to enable reading from and/or writing to the various computer readable media. Mass storage device(s) include removable media and/or non-removable media.

In some embodiments, I/O device(s) may include various devices that allow data and/or other information to be input to or retrieved from computing device. Example I/O device(s) may include cursor control devices, keyboards, keypads, microphones, monitors or other display devices, speakers, printers, network interface cards, modems, lenses, or other image capture devices, and the like.

In some embodiments, interface(s) may include various interfaces that allow computing device to interact with other systems, devices, or computing environments. Example interface(s) may include any number of different network interfaces, such as interfaces to local area networks (LANs), wide area networks (WANs), wireless networks, and the Internet.

In some embodiments, the systems and procedures described herein can be implemented in hardware, or a combination of hardware, software, and/or firmware. For example, one or more application specific integrated circuits (ASICs) can be programmed to carry out one or more of the systems and procedures described herein. The terms "module" or "component" may be intended to convey the implementation apparatus for accomplishing a process, such as by hardware, or a combination of hardware, software, and/or firmware, for the purposes of performing all or parts of operations disclosed herein.

In some embodiments, the present disclosure may be implemented using a system having a camera, a processor, an electronic data storage unit, and a display. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image. The display may include one or more displays for relaying information to the system operators such as a touch screen, computer screen or the like.

In some embodiments, the camera, processor, electronic data storage unit, and digital display are components of a single device. The single device may be a smartphone, tablet, laptop computer, personal digital assistant, or other computing device.

In some embodiments, the sensor may be one or more of the following: temperature, proximity, accelerometer, IR (Infrared), pressure, light (camera), ultrasonic, smoke, gas and alcohol, touch, color, humidity, position, magnetic (hall effect sensor), microphone (sound sensor), tilt, flow and level, pir, and strain and weight sensor.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

Some embodiments may involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, a personal computer microprocessor, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, nonvolatile, dynamic, static, etc.), read-only memory, flash memory, memory caches, or any other tangible, computer-readable storage medium, whether synchronous or asynchronous, emmodies it.

Although the invention is illustrated above, partly with reference to some preferred embodiments, it must be understood that numerous modifications and combinations of different features of the embodiments can be made. All of these modifications lie within the scope of the appended claims.

REFERENCE LIST

100 processing device
103 dental indication
105 status or state detection device
107 generating device
109 code
111 display device
113 data interface
115 detection interface
117 manufacturing material
119 computer
121 data channel
123 device

The invention claimed is:

1. A processing device (100) for processing a dental indication (103), comprising:

an electronic status detection device (105) configured for detecting status data of the processing device (100) comprising at least one of a milling device, a 3D printer, a firing furnace, a press furnace, a sintering furnace, and a post-exposure device and for detecting status of the dental indication (103) comprising a crown, a bridge, a full or partial denture, an implant, an abutment, or a telescopic prosthesis; and an electronic generating device (107) configured for generating a code (109) comprising the status data;

wherein the status data of the dental indication comprises patient data related to the dental indication;

wherein the status data of the processing device comprises an identification number of the processing device, a number of operating hours, a calibration status, error messages and warnings, a process parameter, and an installed software version to provide documentation of relevant status data of the dental indication and the processing device;

wherein the processing device (100) comprises a display device (111) for displaying the code (109) of the processing device and the dental indication;

wherein the display device (111) is configured to display the code (109) of the processing device and the dental indication in an optically detectable or scannable manner; and wherein the status data in the code (109) is summarized in a documentation tool.

2. The processing device (100) according to claim 1, wherein the code comprises a bar code, a QR code, a text code or a machine-readable code.

3. The processing device (100) according to claim 1, wherein the processing device (100) comprises a data interface (113) for electronically sending the code (109).

4. The processing device (100) according to claim 1, wherein the processing device (100) comprises a detection interface (115) for optically detecting data of a manufacturing material (117).

5. A processing system (200), comprising a processing device (100) according to claim 1; and a software application to receive the code (109).

6. A computer program product comprising program code which is stored on a machine-readable medium, the machine-readable medium comprising computer instructions executable by a processor, which computer instructions cause the processor to perform the method according to claim 1.

7. A method of processing a dental indication (103), comprising the steps of:

detecting (S101) status data of a processing device (100) related to the dental indication (103); and generating (S102) a code (109) comprising the status data;

wherein the dental indication comprises a crown, a bridge, a full or partial denture, an implant, an abutment, or a telescopic prosthesis;

wherein the status data of the dental indication comprises patient data;

wherein the status data of the processing device comprises an identification number of the processing device, a number of operating hours, a calibration status, error messages and warnings, a process parameter, and an installed software version;

wherein the processing device comprises at least one of a milling device, a 3D printer, a firing furnace, a press furnace, a sintering furnace, and a post-exposure device;

wherein the processing device (100) comprises a display device (111) for displaying the code (109);

wherein the display device (111) is configured to display the code (109) in an optically detectable or scannable manner; and wherein the status data in the code (109) is summarized in a documentation tool.

8. The method according to claim 7, wherein the code (109) is displayed visually or sent via a data interface (113).

9. The method according to claim 7, wherein the code (109) is transmitted to a data node.

10. The method according to claim 7, wherein the code (109) is stored in an electronic medical record.

11. The method according to claim 7, wherein a plausibility check is performed to determine whether a manufacturing material (117) or machine parameters are suitable for a predetermined dental indication.

* * * * *